(12) United States Patent
Kuiper et al.

(10) Patent No.: US 11,191,636 B2
(45) Date of Patent: Dec. 7, 2021

(54) ELECTROWETTING LENSES HAVING OLEOPHOBIC SURFACES

(71) Applicant: Verily Life Sciences LLC, Mountain View, CA (US)

(72) Inventors: Stein Kuiper, South San Francisco, CA (US); Daniel Otts, Pleasanton, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 231 days.

(21) Appl. No.: 16/107,823

(22) Filed: Aug. 21, 2018

(65) Prior Publication Data

US 2019/0060055 A1 Feb. 28, 2019

Related U.S. Application Data

(60) Provisional application No. 62/548,518, filed on Aug. 22, 2017.

(51) Int. Cl.
*A61F 2/16* (2006.01)
*G02C 7/08* (2006.01)

(52) U.S. Cl.
CPC .......... *A61F 2/1627* (2013.01); *A61F 2/1601* (2015.04); *G02C 7/085* (2013.01); *A61F 2002/1681* (2013.01); *A61F 2250/0001* (2013.01); *A61F 2250/0002* (2013.01); *A61F 2250/0004* (2013.01)

(58) Field of Classification Search
CPC .................. A61F 2/1627; A61F 2/1601; A61F 2002/1681; A61F 2250/0001; A61F 2250/0002; A61F 2250/0004; G02C 7/085
See application file for complete search history.

(56) References Cited

U.S. PATENT DOCUMENTS

| 8,382,280 B2 | 2/2013 | Gupta et al. |
| 8,390,939 B2 | 3/2013 | Henriksen et al. |
| 8,460,376 B2 | 6/2013 | Donitzky et al. |

(Continued)

FOREIGN PATENT DOCUMENTS

| CN | 103797403 A | 5/2014 |
| EP | 1996968 A1 | 12/2008 |

(Continued)

OTHER PUBLICATIONS

International Search Report and Written Opinion of International Application No. PCT/US2018/047418 dated Oct. 24, 2018.

(Continued)

*Primary Examiner* — Jerrah Edwards
*Assistant Examiner* — Tiffany P Shipmon
(74) *Attorney, Agent, or Firm* — McDonnell Boehnen Hulbert & Berghoff LLP

(57) ABSTRACT

An eye-implantable electrowetting lens can be operated to control an overall optical power of an eye in which the device is implanted. A lens chamber of the electrowetting lens contains first and second fluids that are immiscible with each other and have different refractive indexes. By applying a voltage to electrodes of the lens, the optical power of the lens can be controlled by affecting the geometry of the interface between the fluids. To prevent fouling the surface due to folding or other manipulation of the lens during the insertion process, one or more surfaces within the lens chamber is highly underwater oleophobic.

18 Claims, 5 Drawing Sheets

(56) References Cited

U.S. PATENT DOCUMENTS

| | | | |
|---|---|---|---|
| 8,665,526 | B2 | 3/2014 | Pugh et al. |
| 2001/0003162 | A1* | 6/2001 | Chan ............... A61F 2/1645 623/6.23 |
| 2006/0151754 | A1 | 7/2006 | Choi et al. |
| 2006/0244902 | A1 | 11/2006 | Kuiper et al. |
| 2006/0245092 | A1 | 11/2006 | Kuiper et al. |
| 2007/0199454 | A1 | 8/2007 | Bae et al. |
| 2008/0137213 | A1 | 6/2008 | Kuiper et al. |
| 2010/0309560 | A1 | 12/2010 | Dharmatilleke et al. |
| 2012/0050881 | A1 | 3/2012 | Yamazaki et al. |
| 2013/0229618 | A1* | 9/2013 | Otts ............... G02B 26/005 351/159.68 |
| 2013/0258277 | A1 | 10/2013 | Pugh et al. |
| 2013/0335697 | A1* | 12/2013 | Smith ............... G02C 7/04 351/159.04 |
| 2014/0253870 | A1 | 9/2014 | Jiang et al. |
| 2015/0043085 | A1 | 2/2015 | Tsuji |
| 2016/0058553 | A1 | 3/2016 | Salahieh et al. |
| 2016/0129400 | A1 | 5/2016 | Tuteja et al. |

FOREIGN PATENT DOCUMENTS

| | | |
|---|---|---|
| JP | 2001141906 A | 5/2001 |
| JP | 200653433 A | 2/2006 |
| JP | 201268624 A | 4/2012 |
| JP | 2014533373 A | 12/2014 |
| JP | 201693960 A | 5/2016 |
| WO | 2007107589 A1 | 9/2007 |
| WO | 2012166948 A1 | 12/2012 |
| WO | 2016182716 A1 | 11/2016 |

OTHER PUBLICATIONS

Philips S. Brown et al., "Mechanically durable, superoleophobic coatings prepared by layer-by-layer technique for anti-smudge and oil-water separation", Scientific Reports, vol. 5, No. 1, Mar. 3, 2015.

Arun K. Kota et al., "The design and applications of superomniphobic surfaces", NPG Asia Materials, vol. 6, No. 7, Jul. 4, 2014, pp. 1-15.

Nishimoto Shunsuke et al., "Underwater superoleophobicity of a robust rough titanium dioxide surface formed on titanium substrate by acid treatment", Colloids and Surfaces A: Physiochemical and Engineering Aspects, Elsevier, Amsterdam, NL, vol. 464, Oct. 16, 2014, pp. 33-40.

Zhongxin Xue et al., "A Novel Superhydrophilic and Underwater Superoleophobic Hydrogel-Coated Mesh for Oil/Water Separation", Advanced Materials, vol. 23, No. 37, Oct. 4, 2011, pp. 4270-4273.

Saito Tomoya et al., "Facile creation of superoleophobic and superhydrophilic surface by using fluoroalkyl end-capped vinyltrimethoxysilane oligomer/calcium silicide nanocomposites-development of these nanocomposites to environmental cyclical type-fluorine recycle through formation of calcium fluo", Colloid & Polymer Science, vol. 293, No. 1, Sep. 13, 2014, pp. 65-73.

International Search Report and Written Opinion of International Application No. PCT/US2018/017097 dated May 15, 2018.

Mugele et al., "Electrowetting: from basics to applications", Topical Review, Journal of Physics: Condensed Matter, Published Jul. 1, 2005.

B. Berge, "Liquid Lens Technology: Principle of Electrowetting Based Lenses and Applications to Imaging", IEEE, 2005, pp. 227-230.

Lu et al., "Tunable dielectric liquid lens on flexible substrate", Applied Physics Letters 103, 2013.

Mallin, "Flexible Membrane Liquid Lens", Optics & Optoelectronics, 2011 NNIN REU Research Accomplishments.

Li et al., "Fabrication and Characterization of Flexible Electrowettin gon Dielectrics (EWOD) Microlens", NIH Author Manuscript, 2014, 432-441.

Li et al., "Electrowetting-driven variable-foxus microlens on flexible surfaces", Applied Physics Letters 100, 2012.

Eugene Low, "Scientists create clearer glass with permanent, superhydrophilic ceramic coating", Jun. 12, 2014, https://phys.org/news/2014-06-scientists-clearer-glass-permanent-superhydrophilic.html.

Tushna Commissariat, "Textured glass provides a clear view", May 1, 2012, physicsworld, surfaces and interfaces research update, https://physicsworld.com/a/textured-glass-provides-a-clear-view/.

Bico et al., "Rough wetting", Europhysics Letters, 55 (2), pp. 214-220, Jul. 15, 2001.

Li et al., "Three-dimensional surface profiling and optical characterization of liquid microlens using a Shack-Hartmann wave front sensor", Applied Physics Letters 98, 171104 (2011).

Koch et al., "Superhydrophobic and superhydrophilic plant surfaces: an inspiration for biomimetic materials", Phil. Trans. R. Soc. A (2009) 367, 1487-1509.

* cited by examiner

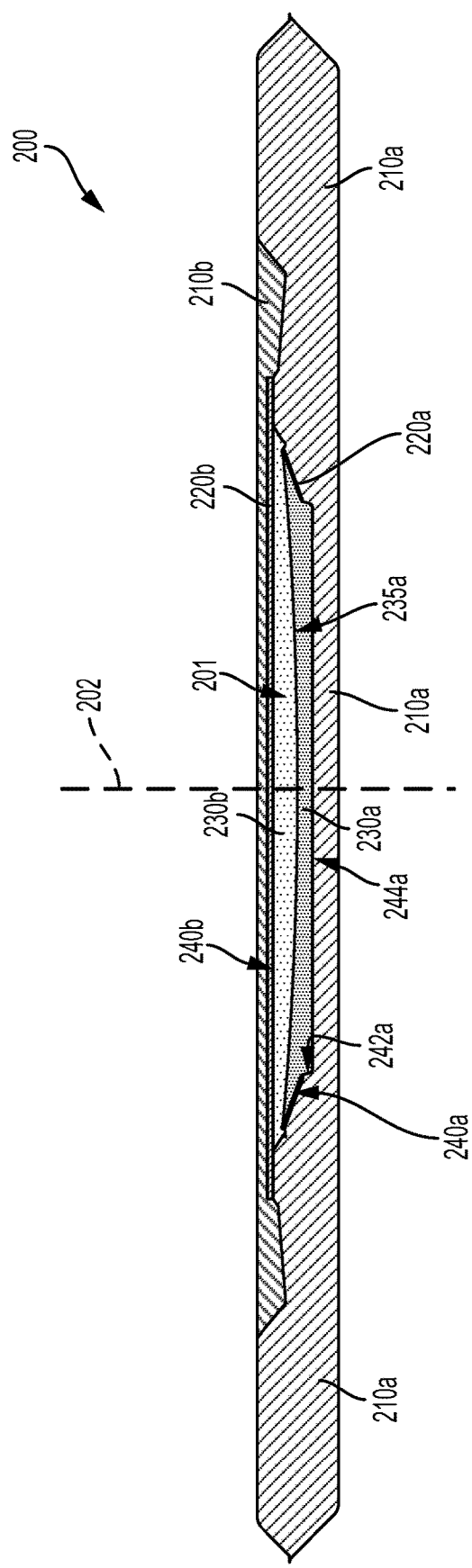
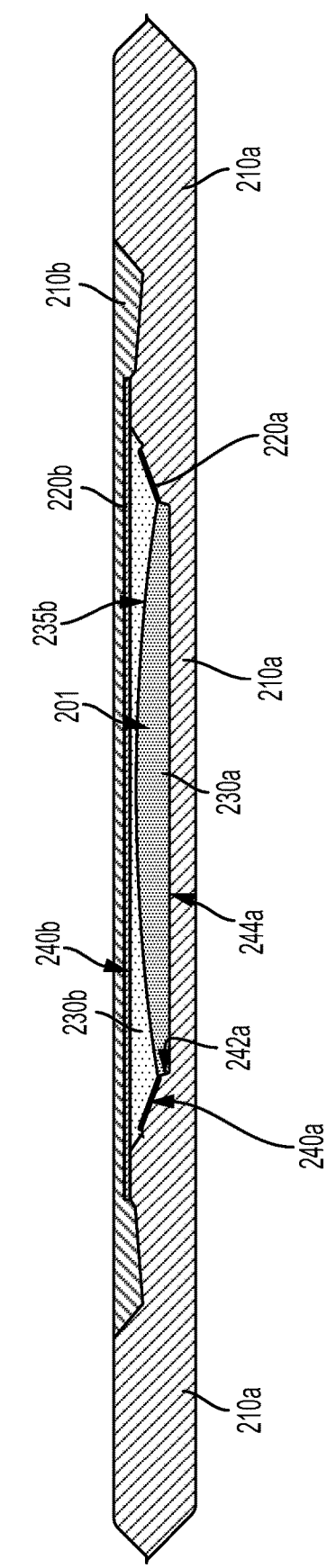
FIG. 2A
FIG. 2B

ELECTROWETTING LENSES HAVING OLEOPHOBIC SURFACES

CROSS REFERENCE TO RELATED APPLICATION

This application claims priority to U.S. Provisional Patent Application No. 62/548,518, filed Aug. 22, 2017, which is hereby incorporated by reference in its entirety.

BACKGROUND

Unless otherwise indicated herein, the materials described in this section are not prior art to the claims in this application and are not admitted to be prior art by inclusion in this section.

Devices can be provided on the surface of the eye and/or within the eye to provide a variety of functions. In some examples, these functions can include functions to improve the ability of a person to view their environment (e.g., to provide an optical correction, to stimulate the retina directly) and/or to present additional visual information to the person (e.g., to present a heads up display or other indications to the person). Such functions can be provided by an intraocular device implanted within the eye (e.g., a retinal implant configured to stimulate the retina to restore vision, a device implanted within the lens capsule to provide a static and/or controllable optical power to the eye).

Such a device can include an adjustable lens to provide an adjustable optical power to the eye. An adjustable lens can operate to provide an adjustable optical power via a variety of processes. In some examples, the adjustable lens can contain two or more immiscible fluids (e.g., an oil and a saline fluid) and the relative locations and/or shapes of the fluids could be controlled to adjust the overall optical power of the immiscible fluids (e.g., by applying an electrical field, by pumping amounts of the fluid into or out of the lens, or by using some other method to control a geometry of an interface between the fluids). However, during normal operation, such fluids could be mixed, could wet improper surfaces within the adjustable lens, or could undergo some other processes resulting in reduced efficacy and/or reduced operational lifetime of the adjustable lens.

SUMMARY

Some embodiments of the present disclosure provide a device that includes an adjustable lens. The adjustable lens includes: (i) a polymeric material, wherein the polymeric material is flexible such that the adjustable lens can be folded or rolled; (ii) an underwater oleophobic layer that is disposed on at least a portion of an internal surface of the polymeric material; (iii) a first fluid that is a polar fluid and that is disposed within the adjustable lens in contact with the underwater oleophobic layer; and (iv) a second fluid that is disposed within the adjustable lens, that is immiscible with the first fluid, and that has a refractive index that differs from a refractive index of the first fluid.

Some embodiments of the present disclosure provide a method including: (i) forming an incision through a cornea of an eye; (ii) inserting an eye-implantable device into the eye through the incision, wherein the eye-implantable device is inserted into the eye in a folded state or a rolled state; (iii) placing the eye-implantable device at a specified location within the eye; and (iv) subsequent to inserting the eye-implantable device into the eye through the incision, unfolding or unrolling the eye-implantable device. The eye-implantable device includes an adjustable lens. The adjustable lens includes: (a) a polymeric material, wherein the polymeric material is flexible such that the adjustable lens can be folded or rolled; (b) an underwater oleophobic layer that is disposed on at least a portion of an internal surface of the polymeric material; (c) a first fluid that is a polar fluid and that is disposed within the adjustable lens in contact with the underwater oleophobic layer; and (d) a second fluid that is disposed within the adjustable lens, that is immiscible with the first fluid, and that has a refractive index that differs from a refractive index of the first fluid.

Some embodiments of the present disclosure provide a device that includes an electrowetting lens. The electrowetting lens includes: (i) a polymeric material, wherein the polymeric material is flexible such that the electrowetting lens can be folded or rolled; (ii) a first fluid that is a polar fluid and that is disposed within the electrowetting lens in contact with an internal surface of the polymeric material; (iii) a first electrode that is disposed on the internal surface of the polymeric material and that is in contact with the first fluid; (iv) a second fluid that is disposed within the electrowetting lens, that is immiscible with the first fluid, and that has a refractive index that differs from a refractive index of the first fluid; (v) a second electrode that is disposed on the internal surface of the polymeric material and that is in contact with at least one of the first fluid or the second fluid; and (iv) a surfactant that is disposed within the first fluid, that is insoluble in the second fluid, and that reduces an interfacial tension between the first fluid and the second fluid.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2A is a side cross-section view of an example eye-implantable device.

FIG. 2B is a side cross-section view of an example eye-implantable device shown in FIG. 2A.

DETAILED DESCRIPTION

Figure 1A:
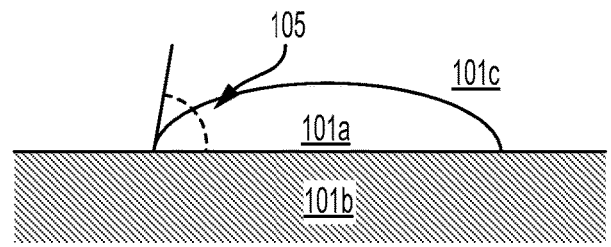
FIG. 1A is a schematic illustration of an example contact angle between a droplet of fluid and a surface.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Implantable devices could be located within an eye of a person to provide a static or adjustable optical power to the eye. Such a static or adjustable optical power could be provided to correct a lack or loss of optical power and/or accommodation in the eye, e.g., to correct for presbyopia, myopia, hyperopia, astigmatism, injury or damage to the eye, removal of the crystalline lens of the eye, or to correct for some other condition of the eye. Such implantable devices could be located within the lens capsule, within the anterior chamber, within the fibrous wall of the eye, proximate to the retina, or in some other location(s) of the eye according to an application. Such an eye-implantable device could include an electronically actuated lens to provide a controllable amount of optical power to the eye. An electronically actuated lens could include an electrowetting lens that includes two or more immiscible fluids whose geometry within the electrowetting lens can be electronically controlled (e.g., by applying an electrical voltage to two or more electrodes of the lens) in order to control an overall optical power of the electrowetting lens. Such an actuated lens could be configured in some other way to control an overall optical power of the lens, e.g., by pumping an amount of one or more immiscible fluids into or out of a lens chamber (e.g., via electrowetting or some other process).

To facilitate implantation of such an eye-implantable device, it can be beneficial for the device to be flexible. Such a flexible device could be bent, folded, or otherwise manipulated to permit implantation. The device could subsequently be unfolded or otherwise manipulated into a flat or otherwise operational state. For example, the eye-implantable device could be rolled up or folded (e.g., in half, in thirds) to facilitate insertion into the eye by way of an incision that is smaller than the unfolded size of the device (e.g., via an incision that is smaller than an unfolded diameter of a lens of the eye-implantable device). Such flexibility could also improve biocompatibility, speed or otherwise improve the process of implantation, permit detection of forces applied to the device, or could provide some other benefit.

However, where such a device includes an electrowetting or otherwise configured lens that contains two or more immiscible fluids, folding or otherwise manipulating the lens can cause the immiscible fluids within the lens to disperse into each other (e.g., the fluids could form an emulsion, a suspension, or some other mixture wherein droplets of one of the fluids are dispersed into the other fluid and/or vice versa), to contact and wet surfaces that they should not come into contact with, or to result in other deleterious effects. For example, when an oil (or other nonpolar fluid) of a lens comes into contact with an interior surface of the lens that is intended to be in contact with saline (or with some other polar fluid) of the lens, the oil can wet and/or foul the interior surface. This wetting and/or fouling can result in decreased clarity or some other deleterious effect on the optical properties and/or functioning of the lens.

To reduce such unwanted effects, the interfacial tensions between the fluids and/or between each of the fluids and internal surfaces of the lens chamber could be controlled. For example, the interfacial tensions between the fluids and a particular surface (e.g., an interior surface of a front window of a lens) could be controlled to facilitate wetting of the particular surface by a first fluid (e.g., a a saline) while preventing wetting of the particular surface by a second fluid (e.g., an oil) and/or facilitating the displacement, by the first fluid, of any amounts of the second fluid that have contacted (e.g., wet) the particular surface. Additionally or alternatively, surfactants or other materials could be added to one or more of the fluids to prevent dispersion of the fluids within each other, to encourage the removal of amounts of the second fluid that may have contacted the particular surface (e.g., by facilitating the formation of droplets of the second fluid), or to otherwise improve the function of the lens.

Controlling the interfacial tensions between a particular surface (e.g., an internal surface of a window or lens that forms part of a lens chamber of a lens) and two or more fluids could include applying a material or treatment to the particular surface. For example, a material that is hydrophilic (e.g., a material that has a contact angle with water that is less than 90 degrees), superhydrophilic (e.g., a material that has a contact angle with water that is approximately 0 degrees), underwater oleophobic (e.g., a material that has a contact angle with an oil, when submerged in water or some other suitable polar fluid (e.g., ethylene glycol), that is greater than 90 degrees), and/or underwater superoleophobic (e.g., a material that has a contact angle with an oil, when submerged in water or some other suitable polar fluid (e.g., ethylene glycol), that is greater than 150 degrees) could be deposited on, formed from, or otherwise disposed on the particular surface. FIG. 1A illustrates an example droplet of fluid 101a deposited on a surface 101b. The environment 101c of the droplet 101a could be vacuum, a gas (e.g., air), or a liquid (e.g., water). The composition of the droplet of fluid 101a, the composition and configuration (e.g., surface texture) of the surface 101b, and the composition of the environment 101c can affect the contact angle 105 between the droplet of fluid 101a and the surface 101b. For example, the surface 101b could be hydrophilic and the droplet 101a could be water such that the contact angle is less than 90 degrees (as illustrated in FIG. 1A). In another example, the surface 101b could be oleophobic (e.g., composed of an oleophobic material and/or having a surface texture or structure that results in oleophobicity), the droplet 101a could be an oil, and the environment 101c could be water. In such an example, the contact angle could be greater than 90 degrees (alternatively, the droplet 101a could be water, the environment 101c could be the oil, and the contact angle with the oleophobic surface 101b could be less than 90 degrees).

Additionally or alternatively, the particular surface could be formed to be porous, to include a plurality of posts or spikes, or to have some other texture or features to facilitate wetting by a first fluid (e.g., a saline or other polar fluid) and/or to prevent wetting by and/or contact with a second fluid (e.g., an oil or other nonpolar fluid). That is, the surface could have a nano-structure or micro-structure that is specified to control the wetting of the surface by the first and/or second fluid. In some examples, the particular surface could have an interfacial tension that is controllable, e.g., by application of an electrical field, by exposure to ultraviolet light, or by some other controlling means. A device containing such a surface could be inserted into an eye, unrolled or unfolded, or otherwise manipulated and subsequently the interfacial tension of the particular surface could be controlled to remove an amount of a fluid that has wetted the surface or to provide some other benefit. Controlling the interfacial tensions between a particular surface and two or more fluids could also include controlling the composition of the fluids, e.g., by adding surfactants or other substances.

The composition, geometry, or other properties of the particular surface could be such that the particular surface is underwater oleophobic, i.e., such that the contact angle of the second fluid, on the particular surface when the particular surface is submerged in water, is greater than 90 degrees, and/or such that the particular surface is underwater superoleophobic, i.e., such that the contact angle of the second fluid, on the particular surface when the particular surface is submerged in water or some other polar fluid (e.g., ethylene glycol), is greater than 150 degrees.

Such eye-implantable devices could include electronics, antennas, voltage regulators, batteries, photovoltaic cells, sensors, or other elements to facilitate operations of the device, e.g., to provide a controllable optical power to an eye. Such eye-implantable devices could receive, from outside of the eye, radio frequency, optical, infrared, acoustic, or other forms of power to power the operations of the device, e.g., from a contact lens, eyeglasses, a head-mountable device, or some other source. The eye-implantable device could receive wireless transmissions to specify an amount of optical power to provide, via controlling the optical power of the lens, to the eye, could operate a sensor to detect a physical variable (e.g., an accommodation force exerted by ciliary muscles of the eye) to specify the amount of optical power to provide, or the eye-implantable device could use some additional or alternative source of information or commands to determine an amount of optical power to provide to an eye.

II. Example Eye-Implantable Device

An eye-implantable device (e.g., an intraocular lens, or IOL) can include electronics and an electronically actuated lens that are operable to provide a controllable optical power (e.g., a controllable diopter, focal length, or other form of optical power or refractive property) to an eye in which the device is implanted. Such an eye-implantable device could include haptics or other formed features, or be formed according to a particular shape, such that the eye-implantable device can be implanted in or at a particular location within an eye, e.g., within the lens capsule of the eye following removal of the crystalline lens, within the anterior chamber of the eye, within the posterior chamber of the eye, along an optical axis of the eye. A controller, battery, antenna, sensors, or other elements can be provided to power the device, to determine a specified amount of optical power to provide to the eye (e.g., based on a sensor output, based on a received wireless command), and to operate the electronically actuated lens to provide such a specified optical power by applying a voltage, current, or other electrical signal to the electronically actuated lens. In some examples, the electronically actuated lens could be an electrowetting lens.

Note that, while reference is made throughout this application to electrowetting lenses of eye-implantable devices, the embodiments provided herein could be applied to other applications. For example, underwater superoleophobic layers could be provided as part of a flexible lens of an eye-implantable device that is configured to control an optical power of the lens via some process other than or in addition to electrowetting. Such a device could be configured to pump one or more immiscible fluids into or out of a lens chamber of a lens using a piezo actuator, an electrowetting actuator, a shape-memory actuator, or other actuator to pump the one or more fluids into or out of the lens chamber. Underwater superoleophobic layers could be provided in non-flexible and/or non-eye-implantable electrowetting lenses or otherwise configured lenses containing two or more immiscible fluids to prevent an oil from wetting or otherwise fouling a surface on which the underwater superoleophobic layer is formed or otherwise disposed, to control the location of a volume of oil within such a device, or to provide some other benefit.

Figure 1B:
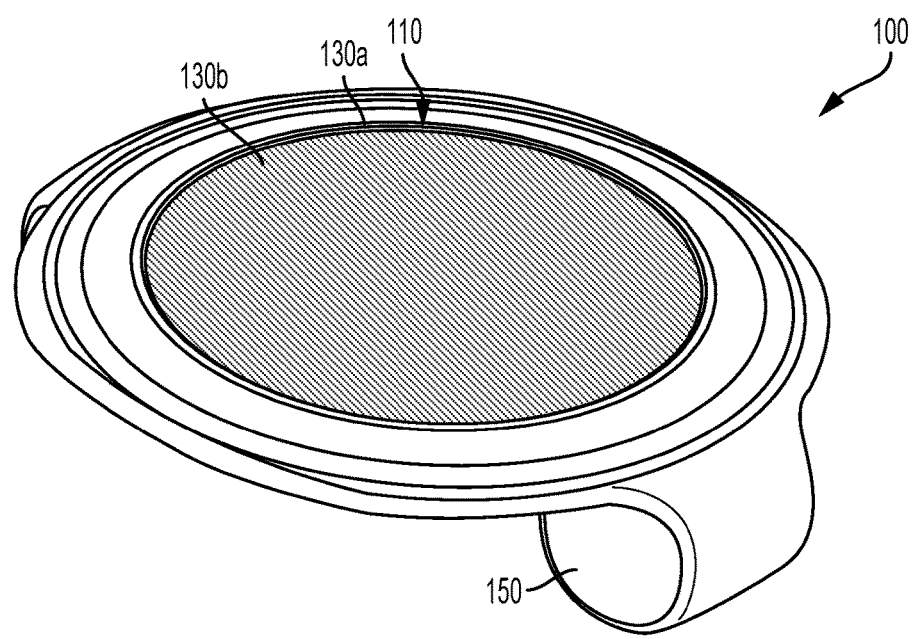
FIG. 1B is a perspective view of an example eye-implantable device.
Figure 1C:
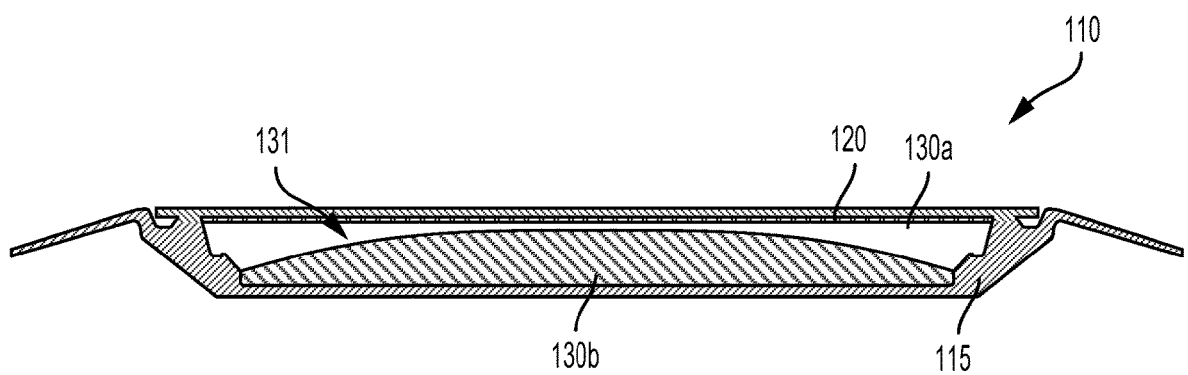
FIG. 1C is a side cross-section view of an electrowetting lens of the example eye-implantable device shown in FIG. 1B.

FIG. 1B is a bottom view of an example eye-implantable device 100. FIG. 1C is a cross-sectional view of an electrowetting lens 110 of the example eye-implantable device 100 shown in FIG. 1B. It is noted that relative dimensions in FIGS. 1B and 1C are not necessarily to scale, but have been rendered for purposes of explanation only in describing the arrangement of the example eye-implantable device 100 and electrowetting lens 110 thereof. The eye-implantable device 100 includes electronics 150 configured to operate the electrowetting lens 110 to provide a controllable optical power and to provide other operations of the eye-implantable device 100. The electronics 150 may include controllers, voltage regulators, antennas, photovoltaic cells, sensors, electrodes, transmitters, receivers, batteries, or other components. The electronics 150 may be configured to receive and/or store wireless energy to power the device 100 (e.g., visible light energy, infrared light energy, radio frequency electromagnetic energy, acoustic energy), to communicate with external devices or systems (e.g., to receive program updates, to receive a commanded optical power level), to detect one or more physical variables (e.g., a light level, a pupil diameter, an intraocular pressure, a voltage related to activity of muscles of the eye, a force exerted by ciliary muscles of the eye, a concentration of one or more substances in the eye) that may be used to determine an optical power to provide or that may be used in some other way, to operate the electrowetting lens 110, or to facilitate some other applications of the device 100.

The electrowetting lens 110 (and/or other elements of the eye-implantable device 100) is formed from a polymeric material 115. The polymeric material can include substantially transparent materials to allow incident light to be transmitted to the retina of the eye through the electrowetting lens 110 of the eye-implantable device 100. The polymeric materials can include biocompatible materials similar to those employed to form implants, vision correction lenses, IOLs, or other implantable devices, such as polyethylene terephthalate ("PET"), polymethyl methacrylate ("PMMA"), silicone hydrogels, rigid, gas-permeable polymeric materials (e.g., oxygen-permeable materials), barrier materials that block diffusion of gases or other substances, combinations of these, etc. The polymeric materials could include flexible and/or foldable water-permeable materials. For example, the polymeric material could include a copolymer comprising 2-phenylethyl acrylate units and 2-phenylethyl methacrylate units. Units of a polymer or copolymer could be cross-linked by an applicable cross-linking agent or unit, e.g., by 1,4-butanediol diacrylate units, 1,6-hexanediol diacrylate units, or some other crosslinking agent or combination of such agents.

The polymeric material 115 defines a lens chamber 131 within which is disposed a first fluid 130a and a second fluid 130b. As shown in FIG. 1C, the lens chamber 131 is defined entirely by the polymeric material 115, which forms a single enclosing element. However, this is intended as a non-limiting example embodiment. The lens chamber 131 may be defined by, and the body of the electrowetting lens 110 may be formed from, a variety of elements (e.g., flat windows, cup-shaped elements, lens-shaped element, ring-shaped elements) formed from a variety of materials (e.g., polymeric materials) via a variety of processes. For example, the lens chamber 131 may be defined by first and second elements formed, respectively, as a cup and a flat lid.

The electrowetting lens 110 could be formed from one or more elements composed of a glass, a polymer (e.g., a water- and/or oxygen-permeable polymeric material), a crystal, or some other material. At least a portion of the electrowetting lens 110 (e.g., a lens, a window or other component that defines at least a part of the lens chamber 131) could be formed from a polymeric material (e.g., one of the polymeric materials listed elsewhere herein) that is permeable to water in aqueous humor of an eye (e.g., from a copolymer comprising 2-phenylethyl acrylate units and 2-phenylethyl methacrylate units cross-linked by 1,4-butanediol diacrylate units).

Flexible and/or foldable polymeric materials may be included in the construction of the device 100 to permit the device 100 to be rolled, folded, or otherwise manipulated such that the device 100 may be inserted through an incision that is smaller than, e.g., the diameter of the unrolled or un-folded electrowetting lens 110. Additionally or alternatively, one or more sealant materials (e.g., a sealant material used to adhere a front window of the electrowetting lens 110 to one or more other elements of the electrowetting lens 110) of the electrowetting lens 110 could be permeable to water in aqueous humor of an eye.

An electrowetting lens and/or a lens chamber thereof as described herein could be constructed from a number of discrete elements (e.g., from a front element, a rear element, and an annular element, from a window element and a cup element). Different elements of such an electrowetting lens could be composed of the same material (e.g., a front window and a cup element of the electrowetting lens 110 could both be composed of a copolymer comprising 2-phenylethyl acrylate units and 2-phenylethyl methacrylate units). Alternatively, elements of an electrowetting lens could be composed of respective different materials (e.g., a front window of the electrowetting lens 110 could be composed of a copolymer comprising 2-phenylethyl acrylate units and 2-phenylethyl methacrylate units and a base, cup-shaped element of the electrowetting lens 110 could be composed of polyethylene terephthalate).

The eye-implantable device 100 may include coating materials disposed on one or more external or internal surfaces of the device, e.g., to improve a biocompatibility of the device, to control a surface energy of an internal surface of the electrowetting lens (e.g., to encourage or prevent wetting of a surface within a lens chamber by one or more fluids within the lens chamber), to prevent passage of ions or other substances, or to provide some other benefit. For example, the electrowetting lens 110 includes an underwater oleophobic layer 120 disposed on an internal surface of the polymeric material 115. The underwater oleophobic layer 120 is configured to prevent the internal surface of the polymeric material 115 (e.g., the internal surface of the front window of the electrowetting lens 110) from being wetted by oils or other nonpolar substances of the second fluid 130b.

Such an underwater oleophobic coating could be formed from a chemical, polymeric material, textured surface or other geometrically specified surface, or other substance disposed on (e.g., adhered to, formed via chemical vapor deposition or some other process) the polymeric material 115. Additionally or alternatively, the underwater oleophobic layer 120 could comprise and/or be formed from the polymeric material 115. For example, the underwater oleophobic layer 120 could comprise posts, channels, or other geometric features or texturing formed into the surface of the polymeric material 115 (e.g., via molding, etching, or some other process). In another example, the underwater oleophobic layer 120 could include an amount of the polymeric material 115 that has been chemically modified by exposure to plasma, chemical etching, or some other process.

The first 130a and second 130b fluid are immiscible (e.g., the first fluid 130a could be saline or some other aqueous fluid and the second fluid 130b could be an oil or some other nonpolar fluid) and differ with respect to refractive index. Thus, a surface of contact between the first 130a and second 130b fluids (e.g., a convex shape, as shown in FIG. 1C) could provide an optical power (e.g., a diopter, a nonzero focal length) related to the difference in the refractive indices of the fluids 130a, 130b and the shape of the surface of contact.

The electrowetting lens 110 further includes at least two electrodes (not shown) disposed on respective internal surfaces of the polymeric material 115 that define the lens chamber 131. Voltages, currents, or other electrical signals can be applied to the at least two electrodes to electronically control the shape of the first 130a and second 130b fluids (e.g., to control a shape of a contact surface between the two fluids 130a, 130b) in order to control an optical power of the electrowetting lens 110. In order to allow the electrowetting lens 110 to be flexed, folded, rolled, or otherwise manipulated during implantation while retaining the functionality of the lens, the electrodes could be composed of gold, aluminum, silver nanowires, or some other material or coating that can be flexed and maintain an overall level of electrical conductivity across the area of the electrodes. Such materials could be applied mechanically (e.g., as a foil) or via some other process (e.g., via sputtering, CVD, PVD, application as a solution followed by evaporation of a solvent of the solution).

One of the first 130a or second 130b fluid may include an aqueous solution. Such an aqueous solution may be electrically conductive, e.g., to facilitate transmission of electrical voltages or currents through the aqueous solution in order to control the shape of the interface between the aqueous solution and another fluid of the electrowetting lens 110. In some examples, the aqueous solution may be substantially isotonic relative to the aqueous humor of an eye into which the eye-implantable device 100 is implanted. The aqueous solution could have an osmolality corresponding to the osmolality of the aqueous humor such that, if the lens chamber is permeable to water in the aqueous humor, a small or substantially zero amount of net water flow occurs between the aqueous solution within the lens chamber and the aqueous humor of the eye. This could include the aqueous solution having an osmolality between 298 milliosmoles per kilogram and 310 milliosmoles per kilogram, or an osmolality between 300 milliosmoles per kilogram and 308 milliosmoles per kilogram, or an osmolality between 302 milliosmoles per kilogram and 306 milliosmoles per kilogram, or an osmolality between 303 milliosmoles per kilogram and 305 milliosmoles per kilogram.

The overall optical power provided by the eye-implantable device 100 and/or the electrowetting lens 110 (e.g., to an eye in which the device 100 is implanted) could be related to the geometry, refractive index, or other properties of elements of the eye-implantable device 100. As noted above, this could include the shape of a contact surface between the first 130a and second 130b fluids within the lens chamber 131 and the refractive indices of the fluids 130a, 130b.

Other elements of the eye-implantable device 100 could provide a static and/or controllable optical power. For example, the front and/or rear surfaces of the electrowetting lens 110 could have curved surfaces to provide an optical power related to a change in refractive index between materials on either side of those surfaces (e.g., between a polymeric material of the electrowetting lens 110 and aqueous humor of an eye, or between the polymeric material and one of the first 130*a* or second 130*b* fluids).

Components of the eye-implantable device 100 and/or electrowetting lens 110 (e.g., windows, cups, annular rings, or other elements defining the lens chamber 131) can be formed to have a curved shape in a variety of ways. For example, techniques similar to those employed to form vision-correction contact lenses and/or intraocular lenses, such as heat molding, injection molding, spin casting, etc. can be employed to form polymeric materials into components of the eye-implantable device 100. Further, an eye-implantable device as described herein could have a different shape from that of the illustrated eye-implantable device 100. For example, an eye-implantable device could include haptics or other formed elements to maintain the eye-implantable device at a particular location within an eye (e.g., within a lens capsule of an eye), to detect accommodation forces exerted by ciliary muscles of an eye, or to provide some other benefit.

Figure 1D:
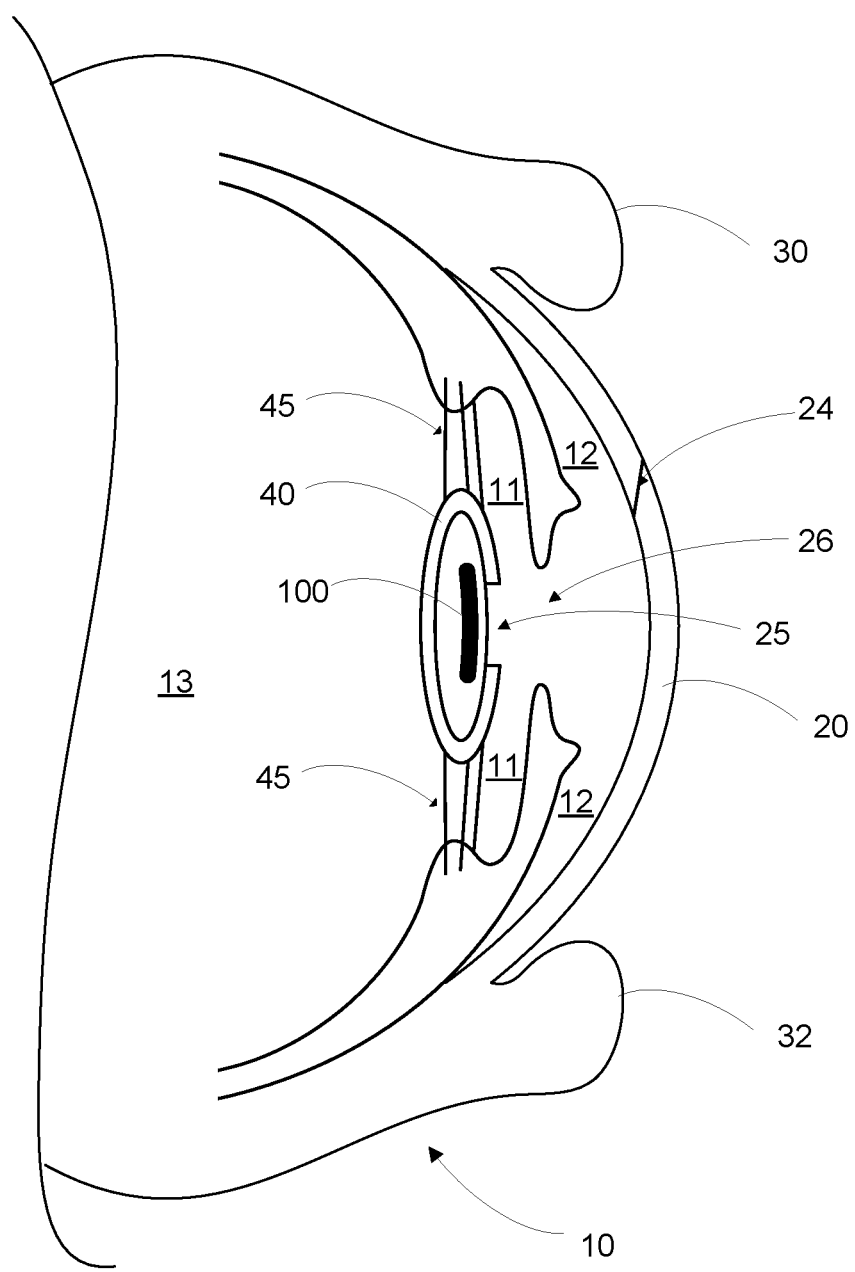
FIG. 1D is a side cross-section view of the example eye-implantable device shown in FIGS. 1B and 1C located within an eye.

FIG. 1D is a side cross-section view of the example eye-implantable device 100 while implanted within an eye 10. The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception.

The light received by the retina is transmitted, in the unaltered eye, through the crystalline lens, being refracted by the lens such that light received from the environment arrives in focus at the retina. The crystalline lens is located within the lens capsule 40 of the eye, which is connected, via the zonules 45, to accommodation muscles (e.g., ciliary muscles) and other elements of the eye. Accommodation forces transmitted through the zonules (e.g., forces generated by the accommodation muscles, forces generated by intrinsic elasticity of the zonules, or forces generated by other sources) act, in the eye, to deform the crystalline lens within the lens capsule 40, controlling the optical power provided by the crystalline lens.

As shown in FIG. 1D, the crystalline lens of the eye 10 has been removed and the eye-implantable device 100 has been surgically emplaced within the lens capsule 40 such that light received by the retina is transmitted through the electrowetting lens 110 of the eye-implantable device 100, being refracted by the electrowetting lens 110 and/or other elements of the eye-implantable device 100. Thus, the eye-implantable device 100 can be operated such that light received from the environment may arrive in focus at the retina, e.g., by operating the electrowetting lens 110 to provide a specified optical power.

The eye-implantable device 100 has been inserted into the eye 10 through an incision 24 formed in the cornea 20 of the eye 10 and then positioned within the lens capsule 40. In order to position the device 100 within the lens capsule 40, a hole 25 has been formed in the lens capsule 40 (e.g., via continuous curvilinear capsulorhexis) and the crystalline lens has been removed (e.g., via ultrasonic phacoemulsification). An eye-implantable device as described herein may be positioned in alternative locations within the eye 10, e.g., within the posterior chamber 11, anterior chamber 12, or in the vitreous humor 13 of the eye 10.

It is noted that relative dimensions in FIG. 1D are not necessarily to scale, but have been rendered for purposes of explanation only in describing the arrangement of the example eye-implantable device 100 within the eye 10. Further, such an implanted device could include multiple elements, located, e.g., in multiple different locations. Such multiple elements could be connected via a cable or by some other means. For example, such an implanted device could include a power reception element and controller that is disposed in the posterior capsule 11 and that is operable to receive wireless power from an eye-mountable device or other external system (not shown) and an electrowetting lens that is disposed within the lens capsule 40 could be operated, by the controller, via a tether connecting the controller and the electrowetting lens, using power from the power reception element.

The eye-implantable device 100 may be rollable, foldable, or otherwise flexible to permit its being rolled, folded, or otherwise manipulated into a smaller shape. This could permit the device 100 to be inserted through a smaller incision through the cornea 20. For example, the device 100 could be rolled up, folded in half, folded in thirds, or manipulated in some other way to permit the device 100 to be inserted through an incision 24 that is less than four millimeters long. In some examples, the device 100 may be rollable, foldable, or otherwise manipulable such that it can be inserted through an incision 24 that is less than 2 millimeters long. In such examples, the eye-implantable device 100 may be unrolled, unfolded, or otherwise manipulated into an operation shape or state (e.g., a substantially flat state) after it is inserted through the incision 24 in the cornea 20 and/or after it has been inserted through some other formed hole or incision (e.g., the hole 25 in the lens capsule) or through some other opening or feature of the eye (e.g., the pupil 26 of the eye 10) to position the device 100 in a specified location of the eye 10.

An electrowetting lens (e.g., 110) as described herein may be configured in a variety of ways such that a shape of two or more immiscible fluids (e.g., a polar fluid and a nonpolar fluid) can be controlled by the application of a voltage, current, or other electrical signal to electrodes of the electrowetting lens. In some examples, this could include applying, via the electrodes, an electrical field that changes the effective surface energy, surface tension, interfacial energy, or other surface properties of one or more surfaces within a lens chamber of such an electrowetting lens such that a first one of the immiscible fluids retreats or advances across the one or more surfaces. As the first fluid retreats or advances across the one or more surfaces, the overall shape of the first fluid, and of a contact surface between the first fluid and a second fluid that is immiscible with the first fluid, may change. If the first fluid and second fluid have differing refractive indices, light may be refracted when passing through the electrowetting lens and an amount of that refraction (and a corresponding optical power of the electrowetting lens) could be related to the shape of the contact surface. Thus, the overall optical power of the electrowetting lens can be electronically controlled by applying electrical signals to the electrodes of the electrowetting lens to, e.g., control the shape of one or more fluids within the electrowetting lens and/or to control a shape of a contact surface between such fluids of the electrowetting lens.

FIG. 2A illustrates a cross-sectional view of an example electrowetting lens 200 during a first period of time. The electrowetting lens 200 includes a lens chamber 201 defined by first 210*a* and second 210*b* elements. In the example electrowetting lens 200, the lens chamber 201 is radially symmetric about a center line 202. A first electrode 220*a* is formed along a first internal surface 244*a* of the electrowetting lens 200 and takes the form of an inclined ring. A second electrode 220b is formed along a second internal surface 240b of the electrowetting lens 200. A first fluid 230a is disposed within the lens chamber 201 and, during the first period of time illustrated in FIG. 2A, is in contact with the first internal surface 240a, the first electrode 220a, a third internal surface 242a of the electrowetting lens 200, and a fourth internal surface 244a of the electrowetting lens 200. A second fluid 230b is also disposed within the lens chamber 201 and is, during the first period of time, in contact with the second internal surface 240b and the second electrode 220b. During the first period of time, a contact surface between the first fluid 230a and the second fluid 230b has a first shape 235a. The first 230a and second 230b fluids are immiscible (e.g., the first fluid 230a is a nonpolar fluid and the second fluid 230b is a polar fluid) and have differing refractive indices.

The electrowetting lens 200, as illustrated in FIGS. 2A and 2B, includes two immiscible fluids (230a, 230b). In some examples, the electrowetting lens 200 could be inserted into an eye (e.g., 10) while containing both fluids 230a, 230b. However, folding, rolling, or otherwise manipulating the electrowetting lens 200 may cause the fluids to disperse into each other, one of the fluids to contact and/or wet a surface that is normally in contact with another of the fluids, or some other unwanted interaction between the fluids and/or surfaces or materials that define the lens chamber 201. Such unwanted interactions may result in fouling of surfaces within the electrowetting lens 200 with one or both of the fluids 230a, 230b, the formation of droplets or foams within the fluids 230a, 230b, a change in the mechanical, chemical or, electrical properties of one or more internal surfaces of the electrowetting lens 200 (e.g., a change in the impedance of an electrode surface), a change in the optical properties of the electrowetting lens 200 (e.g., a blurring of image light passed through the lens 200 due to fouling of one or more surfaces within the electrowetting lens 200), or some other deleterious effects.

To prevent such effects, properties of the fluids 230a, 230b, of the materials defining the lens chamber 201 (e.g., surface coatings disposed on internal surfaces of the electrowetting lens 200), or other elements of the electrowetting lens 200 could be controlled to prevent wetting of particular surface(s) by one of the fluids 230a, 230b, to eject such fluids in the event that such wetting occurs, or to otherwise prevent the deleterious effects described above. This could include specifying the composition of one or both of the fluids 230a, 230b and/or specifying the composition of materials disposed on and/or comprising internal surfaces of the electrowetting lens 200 in order to control the interfacial energy between the fluids 230a, 230b and/or to control the interfacial energy between a particular portion of the internal surface of the electrowetting lens 200 and one or both of the fluids 230a, 230b.

A composition of the fluids 230a, 230b and/or a composition or configuration (e.g., a surface geometry) of the materials defining the lens chamber 201 could be specified to encourage wetting of a particular surface by one of the fluids and/or to discourage wetting of the particular surface by the opposite fluid. For example, the first fluid 230a could be an oil or some other nonpolar fluid, the second fluid 230b could be saline or some other polar fluid, and, to prevent wetting of the second internal surface 240b (e.g., an internal surface of a front window of the electrowetting lens 200) by the first fluid 230a, an underwater oleophobic and/or hydrophilic layer could be disposed on and/or form the second internal surface 240b. Such an underwater oleophobic and/or hydrophilic layer could discourage the formation of droplets of the first fluid 230a on the second internal surface 240b and/or could discourage wetting of the second internal surface 240b by the first fluid 230a. Additionally or alternatively, to prevent wetting of the fourth internal surface 244a (e.g., an internal surface of a rear window of the electrowetting lens 200) by the second fluid 230b, a hydrophobic layer could be disposed on the fourth internal surface 244a.

The likelihood that a particular internal surface of the electrowetting lens 200 may be wetted by a particular one of the first 230a or second 230b fluids may be related to (i) an interfacial energy between the first fluid 230a and the particular internal surface, (ii) an interfacial energy between the second fluid 230b and the particular internal surface, and (iii) an interfacial energy between the first fluid 230a and the second fluid 230b. For example, a particular internal surface of the electrowetting lens 200 (e.g., the second internal surface 240b of the front window of the electrowetting lens 200) could be wetted by a polar second fluid 230b (e.g., a saline) but not by a nonpolar first fluid 230a (e.g., an oil). The probability that the particular internal surface becomes wetted by the first fluid 230a under a particular set of conditions (e.g., following folding or rolling of the electrowetting lens 200) could be related to a relationship between the interfacial energies above according to the following formula:

$$e_{total} = os + sw - ow$$

where $e_{total}$ is the total interfacial energy of the system including the particular surface, the first fluid 230a, and the second fluid 230b, os is the interfacial energy between the first fluid 230a and the second fluid 230b, ow is the interfacial energy between the first fluid 230a and the particular surface, and sw is the interfacial energy between the second fluid 230b and the particular surface. In order to reduce the probability that the particular surface is wetted by the first fluid, $e_{total}$ could be reduced. This could include decreasing sw (e.g., by specifying the composition of the second fluid 230b and/or by disposing a hydrophilic layer on the particular surface), increasing ow (e.g., by specifying the composition of the first fluid 230a and/or by disposing an oleophobic layer on the particular surface), and/or by decreasing sw (e.g., by adding a surfactant to one or both of the fluids 230a, 230b).

In some examples, the particular surface (e.g., 240b) could include an oleophobic layer to increase ow, to decrease sw, or to otherwise prevent wetting of the particular surface by the first fluid 230a or by some other nonpolar fluid. Such an oleophobic layer could include a layer of material disposed on an underlying bulk material, a surface texture formed on the particular surface, a layer of chemically modified material formed from an underlying bulk material, or some otherwise configured layer of oleophobic material.

A coating of hydrophilic, oleophobic, and/or underwater oleophobic material could be disposed on the particular surface to form an underwater oleophobic layer. An underwater oleophobic material could have a contact angle with the first fluid 230a when submerged in water that is greater than 90 degrees; an underwater superoleophobic material could have a contact angle with the first fluid 230a when submerged in water that is greater than 150 degrees. A hydrophilic material could have a contact angle with the second fluid 230b that is less than 90 degrees; a superhydrophilic material could have a contact angle with the second fluid 230b that is approximately 0 degrees.

A layer of a material could have a surface texture or could otherwise exhibit a nano-structure or micro-structure such that the layer has an effective contact angle with oil and/or water that is different than the contact angle with oil and/or water of the material of which the layer is composed. For example, such a material layer could be composed of a material having a contact angle with the first fluid 230a that is greater than 90 degrees and/or having a contact angle with the second fluid 230b that is less than 90 degrees. The layer of the material could include pores, posts, or other textural features such that the effective contact angle of the layer of material with the first fluid 230a, when submerged in water, is greater than 150 degrees or some other angle that is greater than the contact angle of the un-textured material with the first fluid 230a when submerged in water. This difference in effective contact angle could be related to a wetting of the textured surface of the layer by water when submerged in water. Such a layer of textured underwater oleophobic and/or hydrophilic material could be referred to as a textured underwater superoleophobic material.

Such a material could be formed in place on the particular surface (e.g., via chemical vapor deposition, sputtering, polymerization from a solution disposed on the surface, or some other process) or could be a separate formed material adhered to or otherwise disposed on the particular surface. For example, an underwater oleophobic layer could be formed by sputtering or otherwise disposing a layer of silicon dioxide on the particular surface to form an underwater oleophobic layer. In some examples, the underwater oleophobic layer could be formed from an amount of a superhydrophilic material disposed on the particular surface. Such a superhydrophilic material could include titanium dioxide, ceramics, or other superhydrophilic materials. In some examples, the underwater oleophobic layer could include a hydrogel (e.g., poly(acrylic acid) or sodium polyacrylate) formed on the particular surface (e.g., by polymerization from a solution deposited on the particular surface) or otherwise disposed on the particular surface.

Additionally or alternatively, a layer of a polyelectrolyte compound or material could be disposed on the particular surface. Polymer units of such a polyelectrolyte could be zwitterionic. The polyelectrolyte could form zwitterionic brush structures or other structures or textures on the particular surface in order to increase the underwater oleophobicity of the underwater oleophobic layer. This could include forming and/or disposing the zwitterionic elements of the polyelectrolyte on the particular surface such that the zwitterionic elements are perpendicular to the particular surface (e.g., such that the zwitterionic elements form brush structures.

In some examples, a material of an underwater oleophobic layer could become more underwater oleophobic and/or more hydrophilic when exposed to a particular field, illumination, energy, or other specified condition(s). For example, the underwater oleophobic layer could include titanium dioxide and could become more hydrophilic and/or more underwater oleophobic when the titanium dioxide is exposed to ultraviolet illumination. In some examples, the underwater oleophobic layer could be minimally underwater oleophobic or not underwater oleophobic at all in the absence of such applied fields, illumination, energy, or other specified condition(s). In some examples, the underwater oleophobic layer could be formed on or adjacent to one or more electrodes, and the underwater oleophobic layer could become underwater oleophobic, in response to exposure to a current, voltage, electrical field, or other specified condition generated using the one or more electrodes.

A particular surface (e.g., 240b) could include a specified texture or geometry (e.g., posts, pores, ridges) and such a specified texture or geometry could form an underwater oleophobic layer. For example, a plurality of posts, pores, or other features could be formed on or in a surface to increase the overall underwater oleophobicity of the surface. This could occur by reducing an effective contact angle of the particular surface with water, the second fluid 230b, or some other polar fluid; by increasing an effective contact angle of the particular surface with oil, the first fluid 230a, or some other nonpolar fluid; by reducing an area of the particular surface that is not wetted by a polar fluid, by facilitating absorption of polar fluid (e.g., saline) into the particular surface between posts, pores, or other features of the texture or geometry, or by some other mechanism.

A characteristic dimension of such a specified texture or geometry (e.g., a diameter or length of posts, a diameter or length of pores, or some other measure of an element or feature of the texture or geometry) could be specified to reduce an optical effect (e.g., diffraction, dispersion, defocusing, refraction, absorption) of the texture or geometry on visible light passing though the underwater oleophobic layer (e.g., visible light passing through the electrowetting lens 200 to be received by a retina of an eye). For example, such elements or features of the underwater oleophobic layer could have characteristic dimensions less than a wavelength of visible light, e.g., less than 500 nanometers.

In examples wherein the oleophobic layer includes a plurality of posts, such posts could have a cone shape or some other geometry to increase the underwater oleophobicity of the oleophobic layer, e.g., by reducing an area of the particular surface that is not wetted by a polar fluid. An angle, diameter, or other properties of such cones or other posts could be specified to increase the underwater oleophobicity of the underwater oleophobic layer, e.g., by reducing an effective contact angle of the particular surface with respect to water and/or by increasing an effective contact angle of the particular surface with respect to an oil, the first fluid 230a, or some other nonpolar fluid.

An underwater oleophobic layer that includes a texture or geometry could be formed in a variety of ways. In some examples, a textured surface could be formed using a mold to form (e.g., by injection molding or cast molding) the particular surface. In other examples, the surface texture or geometry could be formed by reactive ion etching or other subtractive processes. In yet further examples, a texture or geometry could be formed by using an adhesive to adhere nanoparticles to the particular surface. A porous underwater oleophobic layer could be formed by forming a polymer such that a dissolvable or otherwise removable material is also formed within the polymer; the dissolvable or otherwise removable material can then be removed (e.g., using a solvent), leaving a network of pores within the polymer corresponding to the removable material. For example, a blend of poly(vinylidene fluoride) and poly(methyl methacrylate) could be polymerized to form the underwater oleophobic layer (e.g., by disposing the blend on the particular surface and polymerizing the blend). The composition of the blend could be specified such that the blend exhibits crystallization-induced phase separation, leading to the formation of a network composed of poly(methyl methacrylate) embedded within the poly(vinylidene fluoride). The poly(methyl methacrylate) can then be etched out of the formed material, resulting in a porous, underwater oleophobic layer.

In some examples, an underwater oleophobic layer could be formed on a particular surface of a bulk material by chemically altering the particular surface of the bulk material. This could include exposing a polymeric bulk material (e.g., a polymeric material comprising 2-phenylethyl acrylate units and 2-phenylethyl methacrylate units) to a chemical or physical etching process. For example, such a polymeric material could be exposed to an oxygen plasma in order to oxidize the surface of the polymeric material and to render the surface hydrophilic and/or underwater oleophobic, thus forming an underwater oleophobic layer. In another example, a polymeric material could be exposed to a strong aqueous acid or a strong aqueous base for a specified period of time. Such exposure could partially hydrolyze the polymeric material, forming an underwater oleophobic layer. This could include exposing a polymeric material comprising 2-phenylethyl acrylate units and 2-phenylethyl methacrylate units to a strong aqueous acid or base in order to form, by exposing backbone units of the polymeric material, a high molar mass ionizable hydrogel.

In yet further examples, polar and/or charged molecules could be coupled to the surface of a bulk material (e.g., of a hydrophobic bulk material) in order to form an underwater oleophobic layer. For example, a chlorosilane or methoxysilane could be coupled to the surface of a hydrophobic bulk material (e.g., a bulk material comprising 2-phenylethyl acrylate units and 2-phenylethyl methacrylate units). Such a chlorosilane or methoxysilane could include an alkyl tail or otherwise configured tail to which polar and/or charged moieties are attached, e.g., amino, polyethylene oxide, or epoxy moieties.

In some examples, the composition of one or both of the fluids 230a, 230b could be specified to decrease os, to increase ow, to decrease sw, or to otherwise prevent wetting of a particular surface (e.g., 240b) by the first fluid 230a or by some other nonpolar fluid. Additionally or alternatively, a surfactant could be added to one or both of the polar (e.g., 230b) or nonpolar (e.g., 230a) fluids to reduce an interfacial tension between the polar and nonpolar fluids (e.g., to decrease os). Such a surfactant could operate preferentially at the interface between the polar and nonpolar fluids and/or could not operate at the interface between the nonpolar fluid and the particular surface, e.g., in order to prevent the surfactant from increasing the wettability of the particular surface (e.g., 240b) by the nonpolar fluid (e.g., 230a).

Such a surfactant could be preferentially soluble in the polar fluid (e.g., the surfactant could be insoluble in the nonpolar fluid). Such a preferentially soluble surfactant could be an ionic molecule, e.g., a multivalent ionic molecule. For example, the surfactant could include sodium dodecylsulfate. Additionally or alternatively, the surfactant could include polymeric anionic or cationic surfactants or rheology modifiers. Such polymeric surfactants could form a water-absorbing layer proximate to the particular surface, preventing wetting of the particular surface by the nonpolar fluid. Such polymeric surfactants could include high-HLB-value pluronic surfactants, sodium polyacrylate, sodium caboxymethyl cellulose, poly(2-acrylamido-2-methyl-1-propanesulfonic acid) sodium salt, or other water-soluble high molar mass polymers that comprise ionizable moieties.

As the first 230a and second 230b fluids differ with respect to refractive index, light that passes through the contact surface (e.g., light that is passing through the electrowetting lens 200 along the center line 202) may be refracted. A degree or amount of the refraction, and a related optical power of the electrowetting lens 200, may be related to the shape of the contact surface between the first fluid 230a and the second fluid 230b.

The refractive indices of the two fluids 230a, 230b may differ by a specified amount. The optical power of the electrowetting lens 200 (e.g., the controllable range of optical powers of the electrowetting lens 200) may be related to the magnitude of the difference between the refractive indices. The refractive indices of the two fluids 230a, 230b could differ by more than 0.1. The difference between the refractive indices could be controlled by controlling and/or modifying the refractive index of one or both of the fluids 230a, 230b.

The refractive index of an aqueous fluid (e.g., the second fluid 230b) may be approximately equal to 1.33, the refractive index of water. Alternatively, butanediol or some other substance(s) could be added to such an aqueous solution such that the refractive index of the aqueous solution differs from 1.33. In examples where a substance is added to an aqueous (or other) fluid of the electrowetting lens 200, the lens chamber of the electrowetting lens 200 may include a seal or coating (e.g., could be hermetically sealed) to prevent such a substance from exiting the electrowetting lens 200 and entering the aqueous humor of an eye.

Properties of a nonpolar fluid (e.g., the first fluid 230a) could additionally or alternatively be specified to control the refractive index of the nonpolar fluid. This could include adding substances to the nonpolar fluid. For example, a phenylated silicone oil (e.g., polyphenylmethylsiloxane) could be added to a silicone oil (e.g., to polydimethylsiloxane) to increase its refractive index. Additionally or alternatively, a ratio of components of a nonpolar fluid could be specified to control the refractive index of the nonpolar fluid. For example, a ratio between a first linear alkane (e.g., hexadecane) and a second linear alkane (e.g., nonadecane) could be specified to control the refractive index of the nonpolar fluid. Yet further, a polymer length, a polydispersity, a degree of branching, or some other properties of a nonpolar fluid could be specified to control the refractive index of the nonpolar fluid and/or to control some other property (e.g., melting point, viscosity, surface energy, density) of the nonpolar fluid.

The shape of the contact surface can be controlled by applying an electrical signal to the electrodes 220a, 220b, e.g., by applying an electrical voltage to the electrodes 220a, 220b. The voltage applied to the electrodes 220a, 220b may be related to the steady-state (e.g., following any transient changes in the electrowetting lens resulting from changes in the applied voltage) optical power of the electrowetting lens 200 and/or the shape of the contact surface between the fluids 230a, 230b. The specific relationship could be based on an effect on the surface energy of the first internal surface 240a relative to each of the fluids 230a, 230b, to an effective capacitance between the first electrode 220a and the second electrode 220b via a conductive second fluid 230b (e.g., via a second fluid 230b that includes a conductive, aqueous solution and that is in conductive and/or capacitive electrical contact with the second electrode 220b), or to some other factors.

The first electrode 220a and second electrode 220b could include conductive materials (e.g., aluminum, gold, copper, indium tin oxide, or other materials) disposed on respective internal surfaces of the electrowetting lens 200 (e.g., on surfaces of the first element 210a and second element 210b, respectively). Such deposition could include forming the electrodes in place (e.g., by sputtering, chemical vapor deposition, polymerization, deposition of a carrier fluid containing nanowires or other materials in suspension followed by evaporation of the carrier fluid, by photolithography or other processes for patterning or etching materials in place) and/or forming the electrodes and subsequently disposing them on internal surfaces of the electrowetting lens 200 (e.g., by using an adhesive to adhere a metal foil, wire, rod, cone, textured surface, or other formed conductive material to a surface within the electrowetting lens 200). Additionally or alternatively, one or both of the electrodes 220a, 220b could include wires, rods, cones, textured surfaces, or other elements that are disposed on and/or that penetrate through the internal surface of the electrowetting lens 200 and that protrude into the lens chamber 201.

One or both of the electrodes could further include a dielectric layer disposed between such a conductive material and the inside of the lens chamber 201. For example, the first electrode 220a could include such a dielectric layer. Such a dielectric layer could be provided to prevent large, direct currents from passing from the first electrode 220a into one or both of the first 230a or second 230b fluids, to provide a capacitive electrical coupling between the first electrode 220a and such fluids, to limit an amount of charge that can be transmitting into such fluids via the first electrode 220a, or to provide some other benefits.

Such a dielectric layer could be a separate material (e.g., parylene) deposited on the conductive material (e.g., via CVD, spin coating, or some other process). Additionally or alternatively, the dielectric layer of the first electrode 220a could be formed from the conductive material of the electrode, e.g., the dielectric layer could be a nonconductive layer of aluminum oxide formed by oxidation of an underlying aluminum metal of the first electrode 220a. Such a dielectric layer could be formed via anodization or other electrically-driven reactions at the surface of the electrode. Additionally or alternatively, such a dielectric layer could be formed by redox reactions between the fluids in the lens chamber 201 and the material of the electrode.

In some examples, the formation and/or maintenance of such a dielectric layer could be negatively impacted by the presence of certain ions within the lens chamber 201 (e.g., dissolved in one or both of the fluids 230a, 230b). For example, the presence of chloride ions could act to pit or otherwise damage a dielectric layer of aluminum oxide that has formed on the surface of an aluminum electrode. In such examples, a barrier could be formed from a chloride-impermeable material to prevent chloride ions present in the aqueous humor (or in some other environment to which the lens 200 is exposed) from entering the lens chamber 201 or from entering some other material or volume of the lens 200. Such a material could include a polymeric material, a metal foil or deposited metal layer, or some other material(s). Such materials could be substantially transparent to visible light.

The voltage between the electrodes 220a, 220b could be controlled in order to control the optical power of the electrowetting lens 200 by controlling the shape of the contact surface between the fluids 230a, 230b. FIG. 2B illustrates the electrowetting lens 200 during a second period of time during which a voltage is being applied to the electrodes 220a, 220b such that the contact surface between the first fluid 230a and the second fluid 230b has a second shape 235b. As a result, the optical power of the electrowetting lens 200 during the second period of time is different than the optical power of the electrowetting lens 200 during the first period of time.

The particular shape of the contact surface and/or of the geometry of the fluids 230a, 230b could be related to the applied voltage and to a variety of other factors. Such factors could include the interfacial energy between the fluids 230a, 230b, the interfacial energy between the fluids 230a, 230b and the internal surfaces 240a, 242a, 244a, 240b, the geometry of the internal surfaces 240a, 242a, 244a, 240b, a geometry of the electrodes 220a, 220b, and/or a geometry of a dielectric layer of the first electrode 220a. One or more of these factors could be specified in order to affect the shape of the contact surface between the fluids 230a, 230b, to affect the geometry and/or location of the fluids 230a, 230b within the lens chamber 201, to affect the relationship between an applied voltage and the optical power of the electrowetting lens 200, or to affect some other property of interest of the electrowetting lens 200.

This could include adding surfactants, polar and/or ionic substances, nonpolar substances, to the fluid(s) or otherwise specifying a composition of the first 230a and/or second 230b fluids to control an interfacial energy between the fluids 230a, 230b and/or to control an interfacial energy between the fluids and the internal surfaces 240a, 242a, 244a, 240b of the lens chamber. Additionally or alternatively, the composition of the material composing the internal surfaces 240a, 242a, 244a, 240b could be specified to control the interfacial energy between the internal surfaces and the fluids.

This could include selecting the bulk materials of the first 210a and second 210b elements and/or providing one or more coatings or surface treatments to the internal surfaces of the electrowetting lens 200. For example, the first fluid 230a could be an oil or other nonpolar fluid and one or more of the third 242a or fourth 244a internal surfaces could be superhydrophobic or otherwise hydrophobic. Further, the second fluid 230b could be a polar fluid (e.g., could include a saline solution or other aqueous solution) and the second 240b internal surface could be superhydrophilic or otherwise hydrophilic (e.g., by including a surface coating, by including a surface features or textures, by having been exposed to an oxidization process, or by some other means).

The distribution of such coatings or materials on the internal surfaces of the electrowetting lens 200 and/or the geometry of such surfaces could be specified to center the first fluid 230a along the center line 202 or along some other specified axis of the electrowetting lens 200. This could include applying different coating or other material to internal surfaces according to distance from the center line 202. Additionally or alternatively, a thickness or other property of a dielectric of the first electrode 220a could vary according to distance from the center line 202 such that, when a voltage is applied between the electrodes 220a, 220b, electrical and/or interfacial forces applied to the first 230a and/or second 230b fluids tend to center the first fluid 230a along the center line 202 and/or to conform a boundary between the fluids 230a, 230b on the first internal surface 240a to a circle centered on the center line 202.

The electrowetting lens 200 could be permeable to water or other substances (e.g., ions) in aqueous humor of an eye. This could include the electrowetting lens 200 being composed at least partially of a polymeric material that is permeable to water (or other substances) in the aqueous humor. In examples wherein the lens chamber is permeable to a substance that is present in the aqueous humor, one or both of the fluids 230a, 230b could include a concentration of the substance corresponding to the concentration of the substance in the aqueous humor, e.g., to prevent a net flow of the substance from the aqueous humor into the lens chamber 201 or vice versa.

Additionally or alternatively, the lens chamber could be made impermeable to such substances in the aqueous humor and/or to substances in one or both of the fluids 230a, 230b. For example, one of the fluids could be a conductive fluid that includes butanediol, and the lens chamber could be made impermeable to butanediol and/or could be hermetically sealed. This could include constructing the lens chamber from materials that are impermeable to the substances. Additionally or alternatively, a barrier layer or coating could be formed from such impermeable materials to prevent the substances from entering the lens chamber 201 or some other element or structure of the electrowetting lens 200. For example, a barrier could be formed from a chloride-impermeable material to prevent chloride ions present in the aqueous humor from entering the lens chamber 201 or from entering some other material or volume of the lens 200. Such a material could include a polymeric material, a metal foil or deposited metal layer, or some other material(s). Such materials could be substantially transparent to visible light.

In some examples, components of the electrowetting lens 200 could be composed of a self-healing material. For example, the lens chamber 201 could be at least partially defined by self-healing materials. Such self-healing materials could be provided to maintain the integrity of the lens chamber 201 or of other volumes of the electrowetting lens 200 against bulk fluid flows into or out of such volumes (e.g., between the lens chamber 201 and the aqueous humor of an eye). In some examples, such self-healing materials may be degraded and/or their ability to self-heal diminished by exposure to chloride ions or other substances present in the aqueous humor and/or in the fluids 230a, 230b of the electrowetting lens 200. In such examples, an impermeable material (e.g., a chloride-impermeable material) could be used to form a barrier between the chloride ions or other substances present in the aqueous humor and the self-healing material.

III. Example Electronics of Devices

Figure 3:
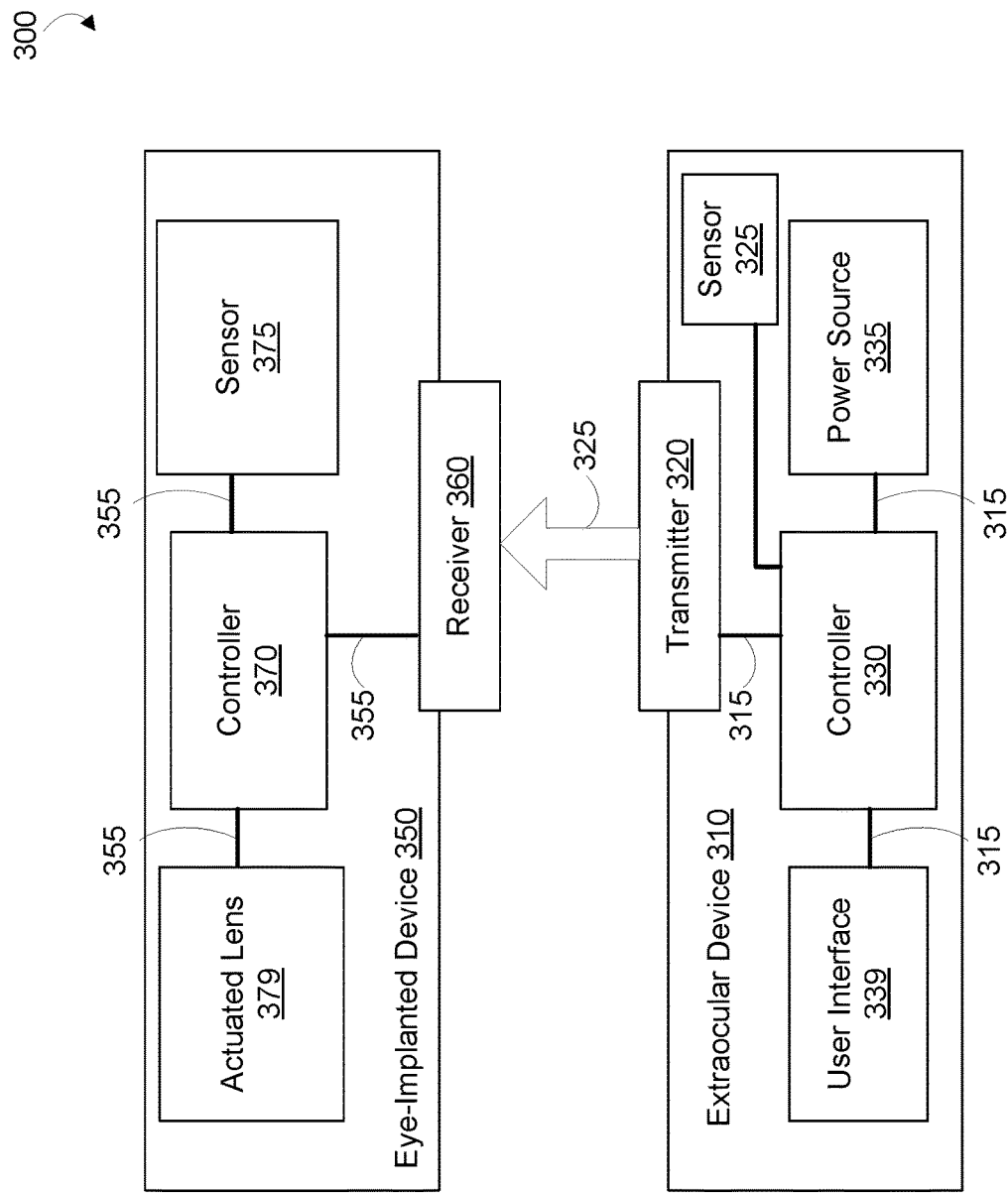
FIG. 3 is a block diagram of an example system that includes an extraocular device that can provide power to an eye-implanted device.

FIG. 3 is a block diagram of a system 300 that includes an extraocular device 310 wirelessly transmitting wireless signals 325 to an eye-implanted device 350. The wireless signals 325 may include wireless power signals to provide power to the eye-implanted device 350, control signals to control the operation of the eye-implanted device 350 (e.g., to control an optical power provided by an actuated lens 379 of the eye-implanted device 350), or other wireless signals. The extraocular device 310 may be a body-mounted device, e.g., a contact lens, a head-mounted display, or some other type of head-mounted device. Additionally or alternatively, the extraocular device 310 may be a handheld device like a cell phone, a device incorporated into furniture, e.g., into a bed to facilitate charging of the eye-implantable device 350 while a user sleeps, or may take some other form(s). The eye-implanted device 350 is implanted on or within an eye of a user.

The extraocular device 310 includes a controller 330, user interface 339, a transmitter 320, a power source 335, and a sensor 325. The transmitter 320 can be operated to wirelessly transmit power, commands, or other signals to the eye-implanted device 350 in an eye. The transmitter 320, the controller 330, the power source 335, the user interface 339, and the sensor 325 can all be connected together via interconnects 315, e.g., via wires, cables and/or, patterns of metallic traces formed on a printed circuit board or other substrate material on which the components may be disposed. Further, the transmitter 320 could comprise metallic traces or patterns formed on such a substrate material (e.g., to form antennas, impedance matching elements, plates of capacitors, electrodes, mirrors or diffraction gratings).

The transmitter 320 can include light-emitting elements (e.g., LEDs, lasers, VCSELs), radio-frequency electromagnetic energy-transmitting elements (e.g., antennas, coils), elements configured to inject a time-varying current into tissues or fluids of a body (e.g., electrodes), or other elements configured to transmit, e.g., power from the power source 335 to the implanted device 350. The transmitter 320 could be configured to control an intensity, a phase, a frequency, a polarization, a direction, or some other properties of wireless signals transmitted from the transmitter 320 to indicate information. The transmitter 320 could be configured to provide power to the eye-implanted device 350 when the extraocular device 310 is not mounted to an eye or body of a user (e.g., when the user is sleeping in a bed such that the eye-implanted device 350 within an eye of the user is proximate to the extraocular device 310) or while the extraocular device 310 is mounted to the eye or body of the user.

The power source 335 may provide power to the extraocular device 310 to, e.g., to recharge a rechargeable battery of the power source 335 in embodiments wherein the extraocular device 310 is an eye-mountable device. The power source 335 could include a battery (e.g., single-use alkaline batteries, rechargeable lithium-polymer batteries), a solar cell, connection to a mains power source, or some other source of energy.

The sensor 325 may be configured to detect physiological properties (e.g., a pupillary diameter of an eye), environmental parameters (e.g., an ambient light level, a distance between eyes of a user and an object at which the user is looking), to detect movements of the eye and/or eyelids of a user (e.g., to detect a vergence of the eyes), or to otherwise detect physical parameters that may be relevant to the operation of the extraocular device 310 and/or the eye-implanted device 350. The user interface 339 may include displays, inputs, speakers, microphones, touchscreens, buttons, scroll wheels, or other elements to facilitate receiving information (e.g., commands) from a user and/or to provide information (e.g., a command interface, a battery status or other information about the devices 310, 350) to a user. For example, the user interface 339 may be operated to receive commands from a user related to a desired optical power of the eye-implanted device 350 and/or information about a distance a user wishes to see or some other information related to an optical power that could be desired from the eye-implanted device 350.

The eye-implanted device 350 includes a controller 370, a sensor 375, a receiver 360, and an actuated lens 379. The actuated lens 379 could be an electrowetting lens as described herein. The receiver 360 can be operated to receive power or other wireless signals 325 wirelessly transmitted by the transmitter 320 (e.g., from the power source 335 of the extraocular device 310). This could include receiving optical signals (e.g., via a photovoltaic cell, photodiode, or other light-sensitive elements), radio frequency electromagnetic signals (e.g., via an antenna, via a coil), an electrical current or potential in the tissues or fluids surrounding the eye-implanted device 350 (e.g., via electrodes), or receiving some other signals wirelessly transmitted from the extraocular device 310. The eye-implanted device 350 could include a capacitor, a battery, or other type of energy storage device to provide energy for use by the device 350 when power is unavailable from the other systems (e.g., when the extraocular device 310 is not mounted to or otherwise proximate to the eye-implanted device 350).

The sensor 375 is configured to detect a physiological property of the body (e.g., a pressure or force, a biopotential, a light intensity). In a particular example, the sensor 375 could be an accommodation sensor configured to detect, directly or indirectly, accommodation forces exerted on a lens capsule of the eye, e.g., by detecting a force or pressure within the lens capsule via haptics, via an elastic material disposed in the lens capsule, via detection of electrical activity of the ciliary muscles, or via some other means.

The actuated lens 379 is operable to control an optical power that is provided to the eye by the actuated lens 379. Operating the actuated lens 379 to control the optical power of the lens could include applying a voltage to a liquid crystal of the lens 379, applying a voltage to electrodes of an electrowetting actuated lens 379 or operating a pump or some other element to control a pressure and/or disposition of a fluid within the lens 379, or controlling the optical power of the lens by some other method.

The eye-implanted device 350 and/or extraocular device 310 could include additional or alternative elements, and could include more or fewer elements than those illustrated in FIG. 3. This could include the eye-implanted device 350 including elements configured to transmit wireless signals to the extraocular device 310 and the extraocular device 310 including elements configure to receive such transmitted signals. In such an example, the eye-implanted device 350 and the extraocular device 310 could additionally include a transmitter and receiver, respectively. Additionally or alternatively, the illustrated receiver 360 and transmitter 320 could be configured as transceivers to facilitate bidirectional communication and/or to share one or more elements (e.g., antennas, filters, coils, power conditioning systems) in common with other elements configured to facilitate bidirectional communication.

It is noted that the block diagram shown in FIG. 3 is described in connection with functional modules for convenience in description. However, embodiments of the extraocular device 310 and/or eye-implanted device 350 can be arranged with one or more of the functional modules ("sub-systems") implemented in a single chip, integrated circuit, and/or physical feature. That is, the functional blocks in FIG. 3 need not be implemented as separated modules. Moreover, one or more of the functional modules described in FIG. 3 can be implemented by separately packaged chips or other components electrically connected to one another. Further, note that an extraocular device and/or an eye-implantable device as described herein could include additional or alternative components to those shown in FIG. 3 (e.g., additional sensors, actuated lenses, displays, retinal stimulator arrays, electrodes, batteries, controllers, transmitters, receivers, stimulators, etc.). For example, the power source 335 of the extraocular device 310 could be a single-use battery and the extraocular device 310 could be operated as a single-use device (e.g., operated until the battery of the power source 335 is depleted and then discarded and/or recycled).

IV. Example Methods

Figure 4:
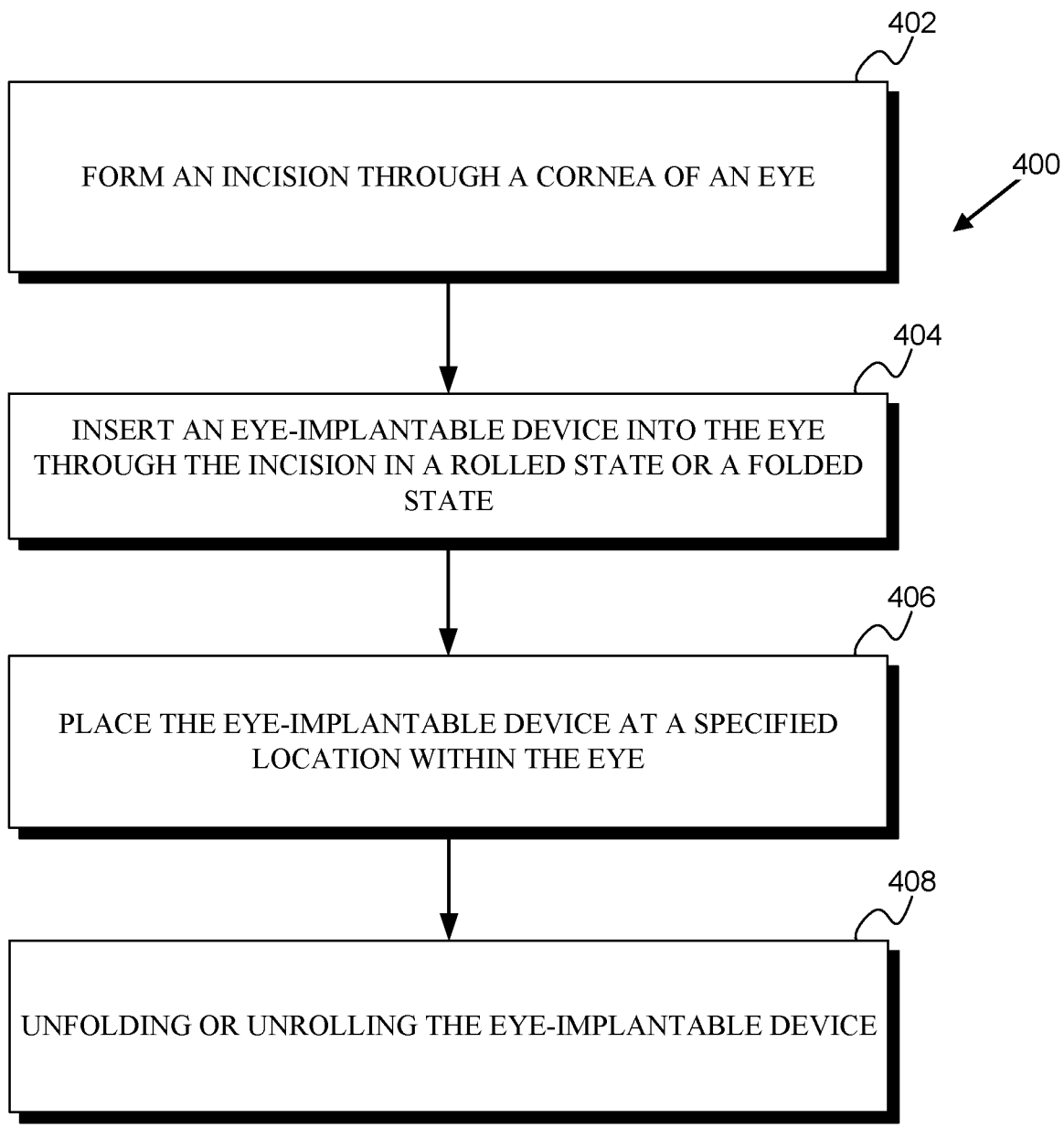
FIG. 4 is a flowchart of an example process.

FIG. 4 is a flowchart of a method 400 for implanting an eye-implantable device as described herein within a human eye. The device includes an electrowetting lens as described herein that includes (i) a lens chamber that has an internal surface and that is flexible, such that the lens chamber may be folded or rolled, (ii) a first fluid that is disposed within the lens chamber in contact with the internal surface and that comprises a polar fluid, (iii) a first electrode that is disposed on the internal surface of the lens chamber in contact with the first fluid, (iv) a second fluid that is disposed within the lens chamber, that is immiscible with the first fluid, and that differs from the first fluid with respect to refractive index; and (v) a second electrode that that is disposed on the internal surface of the lens chamber in contact with at least one of the first fluid or the second fluid. The electrowetting lens may include further elements. For example, the electrowetting lens could include an underwater oleophobic layer disposed on at least a portion of the internal surface. Additionally or alternatively, the electrowetting lens could include a surfactant that is disposed within the first fluid, that is insoluble in the second fluid, and that reduces an interfacial tension between the first fluid and the second fluid.

The method 400 includes forming an incision through the cornea of an eye (402). This could include operating a scalpel, a laser, a diamond blade, a metal blade, or some other instruments to create an incision through the cornea. The incision could be created by creating multiple separate cuts or incisions into the cornea. For example, a first cut could be made perpendicular to the surface of the sclera, and one or more subsequent cuts could be made at other angles (e.g., tangential angles) relative to the sclera. The incision could be formed to be water-tight, to cause a minimum of astigmatism, or to satisfy some other considerations. The formation of the incision could be accompanied by mechanical stabilization of the eye (e.g., using fixation rings, forceps, or other means), administration of topical or global anesthesia, or some other steps. The formed incision could have a length or other dimension within some specified range; e.g., the incision could be less than 4 millimeters long, or less than 2 millimeters long.

The method 400 includes inserting the eye-implantable device into the eye through the incision (404). Inserting the eye-implantable device into the eye includes inserting the eye-implantable device in a folded or rolled state (e.g., in a state wherein the electrowetting lens of the eye-implantable device is folded and/or rolled). In some examples, the eye-implantable device could be received in such a folded or rolled state (e.g., the eye-implantable device could be provided by a manufacturer in a folded or rolled state within a sterile pouch or other packaging). Alternatively, the eye-implantable device could be provided in a flat state or other configuration and the method 400 could include folding or rolling the eye-implantable device prior to insertion (e.g., using forceps or other instruments to fold or roll the device, using a purpose-built device to fold or roll the eye-implantable device).

Inserting the eye-implantable device into the eye through the incision could include using forceps or some other means to insert the eye-implantable device through the incision. Additionally or alternatively, the eye-implantable device could include tabs, rods, or other features to facilitate such insertion. Such features could be later removed from the eye-implantable device (e.g., by cutting, crimping, laser cutting, or some other means) or could remain as part of the eye-implantable device following implantation. The eye-implantable device could be inserted as multiple components (e.g., multiple components connected via one or more cables or other connecting means).

The method 400 further includes placing the eye-implantable device at a specified location within the eye (406). As noted above for insertion of the eye-implantable device through the incision, this could include using instruments to manipulate and position the eye-implantable device and/or using tabs, rods, or other features of the eye-implantable device. Placing the eye-implantable device at the specified location could include inserting the device through additional incisions or other surgically formed features of the eye (e.g., an incision through the iris, through a hole formed in the lens capsule of the eye) and/or through natural features of the eye (e.g., through the pupil of the iris). The specified location could be within the lens capsule, in the anterior capsule, in the posterior capsule, in the vitreous humor, or in some other location of the eye. Placing the eye-implantable device at the specified location could include manipulating haptics or other features of the device and/or additional implanted elements in order to secure the device at the specified location, to facilitate interactions between the device and the eye (e.g., to facilitate detection of accommodation forces applied to the lens capsule of the eye), or to provide some other benefit. Placing the eye-implantable device at the specified location could include assembling multiple different elements of the device together, e.g., assembling an electrowetting lens together with an electronics module to form the eye-implantable device.

The method 400 further includes, subsequent to inserting the eye-implantable device into the eye through the incision, unfolding or unrolling the eye-implantable device (408). This could include unfolding or unrolling the electrowetting lens of the eye-implantable device, or unfolding and/or unrolling additional elements of the eye-implantable device. Forceps, purpose-built devices, or other instruments could be used to unfold or unroll the eye-implantable device. In some examples, a jig, plane, or other instrument could be used to facilitate unrolling or unfolding of the eye-implantable device such that, once unfolded or unrolled, the electrowetting lens of the eye-implantable device is flat or such that the electrowetting lens conforms to some other specified shape. In some examples, unfolding or unrolling the eye-implantable device could include removing a clamp, band or other restraint from the device, releasing the device from a needle or other instrument that is enclosing or otherwise restraining the device, or otherwise releasing a pressure or force that is applied to the eye-implantable device and that prevents the eye-implantable device from unfolding or unrolling.

The method 400 could include additional steps or elements in addition to those depicted in FIG. 4. For example, the method 400 could include exposing the electrowetting lens to electromagnetic radiation, heat, or other energy to remove an amount of one of the fluids from a particular surface within the lens chamber (e.g., to remove an amount of an oil from inside a window or form some other surface that has been fouled by or that has otherwise come into contact with the oil). In some examples, an underwater oleophobic layer comprising titanium dioxide could be disposed on at least a portion of the internal surface of the lens chamber and the titanium dioxide could be exposed to ultraviolet illumination to facilitate removal of the second fluid, or of some other fluid, from the surface on which the titanium dioxide is disposed. Additionally or alternatively, the eye-implantable device could be operated to remove a fluid from one or more surfaces within the lens chamber (e.g., to remove an oil from the first electrode) or to otherwise manipulate the disposition of the first and/or second fluids within the lens chamber (e.g., to center a droplet of the second fluid along an optical axis of the lens chamber). This could include applying a voltage between the first and second electrodes, or between one or both of the first and second electrodes and one or more further electrodes.

In some examples, the method 400 could include adding or removing materials or fluids to or from the lens chamber of the eye-implantable device, e.g., adding or removing an amount of the first fluid. This could be performed using one or more needles, one or more tubes connected between the device and external systems, or via some other method. For example, the lens chamber could be rinsed by introducing an amount of the first fluid into the lens chamber, e.g., via the needle, via one or more further needles, via the tube, via one or more further tubes, or via some other means. Additionally or alternatively, an amount of the first fluid could be removed from the lens chamber, e.g., by applying suction via the needle, tube, or other fluid transfer means. The method 400 could include removing gases from such fluids prior to introducing such fluids into the lens chamber.

The method 400 could include further surgical manipulations of the eye, e.g., the formation of a hole in the lens capsule and/or the removal of the crystalline lens, the removal of a previously implanted device (e.g., a static IOL). The method 400 could include programming and/or testing an eye-implantable device. In some examples, the eye-implantable device could be implanted through the sclera or via some other route, and the method 400 could include forming alternative incisions (e.g., through the sclera) and inserting the device through such alternative incisions.

V. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. For example, adjustable lenses as described herein could be included in devices that are not eye-implantable and not intended for use while mounted to an eye (e.g., in cameras, scientific equipment, etc.). It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A device comprising:
an adjustable lens, wherein the adjustable lens comprises:
a polymeric material, wherein the polymeric material is flexible such that the adjustable lens can be folded or rolled;
an underwater superoleophobic layer, wherein the underwater superoleophobic layer is disposed on at least a portion of an internal surface of the polymeric material;
a first fluid, wherein the first fluid is a polar fluid, and wherein the first fluid is disposed within the adjustable lens in contact with the underwater superoleophobic layer, wherein an amount of the first fluid is adsorbed onto the underwater superoleophobic layer thereby wetting the underwater superoleophobic layer; and
a second fluid, wherein the second fluid is disposed within the adjustable lens, wherein the second fluid is immiscible with the first fluid, wherein a refractive index of the second fluid differs from a refractive index of the first fluid, and wherein the underwater superoleophobic layer has a contact angle with the second fluid, when the underwater superoleophobic layer is submerged in water and wetted by an amount of water, that is greater than 150 degrees.

2. The device of claim 1, wherein the lens is an electrowetting lens, and wherein the device further comprises:
a first electrode, wherein the first electrode is disposed on the internal surface of the polymeric material in contact with the first fluid; and
a second electrode, wherein the second electrode comprises a dielectric layer, and wherein the second electrode is disposed on the internal surface of the polymeric material and is in contact with at least one of the first fluid or the second fluid.

3. The device of claim 1, wherein the underwater superoleophobic layer comprises a plurality of posts.

4. The device of claim 1, wherein the underwater superoleophobic layer is porous.

5. The device of claim 1, wherein the underwater superoleophobic layer comprises a portion of the polymeric material that has been chemically altered to be underwater superoleophobic.

6. The device of claim 1, wherein the underwater superoleophobic layer comprises titanium dioxide.

7. The device of claim 1, wherein the superoleophobic layer comprises a superhydrophilic material.

8. The device of claim 1, wherein the superoleophobic layer comprises a hydrogel.

9. The device of claim 1, further comprising a surfactant, wherein the surfactant is disposed within the first fluid, wherein the surfactant is substantially insoluble in the second fluid, and wherein the surfactant reduces an interfacial tension between the first fluid and the second fluid.

10. The device of claim 9, wherein the surfactant comprises an ionic molecule.

11. The device of claim 10, wherein the surfactant comprises sodium dodecylsulfate.

12. A method comprising:
forming an incision through a cornea of an eye;
inserting an eye-implantable device into the eye through the incision, wherein the eye-implantable device comprises:
an adjustable lens, wherein the adjustable lens comprises:
a polymeric material, wherein the polymeric material is flexible such that the adjustable lens can be folded or rolled;
an underwater superoleophobic layer, wherein the underwater superoleophobic layer is disposed on at least a portion of an internal surface of the polymeric material;
a first fluid, wherein the first fluid is a polar fluid, and wherein the first fluid is disposed within the adjustable lens in contact with the underwater superoleophobic layer, wherein an amount of the first fluid is adsorbed onto the underwater superoleophobic layer thereby wetting the underwater superoleophobic layer; and
a second fluid, wherein the second fluid is disposed within the adjustable lens, wherein the second fluid is immiscible with the first fluid, wherein a refractive index of the second fluid differs from a refractive index of the first fluid, and wherein the underwater superoleophobic layer has a contact angle with the second fluid, when the underwater superoleophobic layer is submerged in water and wetted by an amount of water, that is greater than 150 degrees;
wherein inserting the eye-implantable device into the eye through the incision comprises inserting the eye-implantable device in a folded state or a rolled state;
placing the eye-implantable device at a specified location within the eye; and
subsequent to inserting the eye-implantable device into the eye through the incision, unfolding or unrolling the eye-implantable device.

13. The method of claim 12, wherein the incision is less than 4 millimeters long.

14. The method of claim 12, wherein the underwater superoleophobic layer comprises titanium dioxide, and wherein the method further comprises exposing the underwater superoleophobic layer to ultraviolet illumination.

15. The method of claim 12, wherein the lens is an electrowetting lens, and wherein the eye-implantable device further comprises:
a first electrode, wherein the first electrode is disposed on the internal surface of the polymeric material in contact with the first fluid; and
a second electrode, wherein the second electrode comprises a dielectric layer, and wherein the second electrode is disposed on the internal surface of the polymeric material in contact with at least one of the first fluid or the second fluid.

16. A device comprising: an electrowetting lens, wherein the electrowetting lens comprises:
a polymeric material, wherein the polymeric material is flexible such that the electrowetting lens can be folded or rolled;
a first fluid, wherein the first fluid is a polar fluid, and wherein the first fluid is disposed within the electrowetting lens in contact with an internal surface of the polymeric material;
wherein an amount of the first fluid is adsorbed onto the underwater superoleophobic layer thereby wetting the underwater superoleophobic layer;
a first electrode, wherein the first electrode is disposed on the internal surface of the polymeric material and in contact with the first fluid;

a second fluid, wherein the second fluid is disposed within the electrowetting lens, wherein the second fluid is immiscible with the first fluid, and wherein a refractive index of the second fluid differs from a refractive index of the first fluid;

an underwater superoleophobic layer disposed on at least a portion of an internal surface of the polymeric material, wherein the underwater superoleophobic layer has a contact angle with the second fluid, when the underwater superoleophobic layer is submerged in water, that is greater than 150 degrees;

a second electrode, wherein the second electrode comprises a dielectric layer, and wherein the second electrode is disposed on the internal surface of the polymeric material and in contact with at least one of the first fluid or the second fluid; and a surfactant, wherein the surfactant is disposed within the first fluid, wherein the surfactant is substantially insoluble in the second fluid, and wherein the surfactant reduces an interfacial tension between the first fluid and the second fluid.

17. The device of claim 16, wherein the surfactant comprises an ionic molecule.

18. The device of claim 17, wherein the surfactant comprises sodium dodecylsulfate.

* * * * *